US012508407B2

(12) United States Patent
Piscitelli

(10) Patent No.: US 12,508,407 B2
(45) Date of Patent: Dec. 30, 2025

(54) SURGICAL DEVICE FOR CEREBRAL HERNIATION

(71) Applicant: Claudia Piscitelli, Anagni (IT)

(72) Inventor: Claudia Piscitelli, Anagni (IT)

( * ) Notice: Subject to any disclaimer, the term of this patent is extended or adjusted under 35 U.S.C. 154(b) by 301 days.

(21) Appl. No.: 18/486,488

(22) Filed: Oct. 13, 2023

(65) Prior Publication Data

US 2024/0123203 A1 Apr. 18, 2024

(30) Foreign Application Priority Data

Oct. 13, 2022 (IT) ........................ 102022000021135

(51) Int. Cl.
*A61M 27/00* (2006.01)
*A61M 1/00* (2006.01)
*A61M 25/00* (2006.01)

(52) U.S. Cl.
CPC ............ *A61M 27/006* (2013.01); *A61M 1/74* (2021.05); *A61M 25/0012* (2013.01)

(58) Field of Classification Search
CPC ............ A61M 1/73; A61M 1/74; A61M 1/85; A61M 1/87; A61M 2202/0464; A61M 2205/3303; A61M 2205/3324; A61M 2205/3344; A61M 2205/3368; A61M 2210/0693; A61M 25/0012; A61M 27/006; A61B 5/031
See application file for complete search history.

(56) References Cited

U.S. PATENT DOCUMENTS

| | | | | |
|---|---|---|---|---|
| 4,767,400 A | 8/1988 | Miller et al. | | |
| 2013/0165821 A1* | 6/2013 | Freedman | ........... | A61M 3/0279 604/20 |
| 2015/0112289 A1 | 4/2015 | Stebbins et al. | | |
| 2021/0187257 A1 | 6/2021 | Khanna | | |
| 2021/0267762 A1 | 9/2021 | Sampath et al. | | |
| 2022/0062601 A1 | 3/2022 | Morse et al. | | |

OTHER PUBLICATIONS

Italian Search Report issued Apr. 24, 2023, in corresponding Italian Application No. 102022000021135, 9 pages (partial English translation provided).

* cited by examiner

*Primary Examiner* — Kai H Weng
(74) *Attorney, Agent, or Firm* — Maier & Maier, PLLC

(57) ABSTRACT

A surgical device for cerebral herniation including a structure adapted to cover the skullcap, the structure including a first portion to provide the structure with its shape a second portion to be in contact with the cerebral parenchyma, and a plurality of tubular canals forming a lattice that subdivides the surgical device in areas corresponding to respective areas of the cerebral surface, a plurality of sensors attached to the second portion of the structure and in contact with the cerebral parenchyma, the sensors monitoring one or more parameters of the brain, an outflow system including at least one drainage catheter and a connection to an aspiration system, the outflow system positioned along the perimeter of the structure to convey waste liquids or blood outside, and the plurality of tubular canals include a plurality of administration canals, the tubular canals including an inlet extremity and an outlet extremity.

9 Claims, 2 Drawing Sheets

SURGICAL DEVICE FOR CEREBRAL HERNIATION

FIELD

The present invention relates to a surgical device for cerebral herniation.

In particular, the object of the present invention is a surgical device for brain herniation applicable after craniectomy or cranioresection.

BACKGROUND

As is known, cerebral herniation is a pathological phenomenon, due to an increase in intracranial pressure, which causes abnormal protrusion of brain tissue. As a result, brain tissue, cerebrospinal fluid, and blood vessels are moved, or pressed, relative to their usual position in the head. If this were to happen during surgery, the success of the surgery would also be questioned. In fact, brain herniation, as a whole, represents a potentially deadly event.

In addition, it is possible to classify brain hernias into several types, depending on the part of the brain affected:

- subfalcial: dislocation of the brain tissue on the corneal plane, in a laterolateral direction, due to a mass that pushes the girdle of the crawler under the scythe. One or both of the anterior cerebral arteries remain trapped, causing a heart attack of the paramedic cortex. This is the most common type of cerebral hernia.
- transtentorial or uncal: the uncus is pushed towards the free margin of the cerebral Tentorium (membrane), laterally dislocating the midbrain and the subtalamo against the free margin opposite. Tentorium compresses the contralateral cerebral peduncle, resulting in a hemiparesis homolateral to the lesion (often causing localization errors). Often an occlusive hydrocephalus is associated by compression of the Silvio aqueduct. It is the most frequent and clinically relevant type of cerebral hernia. In addition, transtentorial herniations can involve both the temporal lobe, causing uncal syndrome, both the cerebellum, and the structures of the brainstem, causing central syndrome.
- central: both temporal lobes move through an opening in the Tentorio, called the tentorial notch, or tentative incisor.
- hernia upwards: subdtentorial dislocation that compresses the brain stem, deforming it and causing areas of ischemia in the trunk itself.
- tonsil hernia: dislocation of the cerebellar hemispheres (especially the tonsil) in the infratentorial area, through the large occipital foramen (Downward hernia), which goes to compress the medulla oblongata. May cause internal hydrocephalus and severe bulb injury with lethal outcome. It is often associated with tumors of the posterior cranial fossa.

The main cause of a cerebral hernia is cerebral edema, an alteration of the central nervous system by accumulation of intracellular and extracellular fluids, which leads to an increase in brain volume and pressure. In addition, brain hernias are the most common side effect of brain tumors (e.g. primary brain tumor, such as meningiomas and glioblastomas and metastatic tumors) but may also be caused by abscess, hydrocephalus, stroke, or be a consequence of cranial neurosurgery.

The most common symptoms of the onset of cerebral herniation are: progressive loss of consciousness, loss of reflexes of the brain stem, irregular breathing, cardiac arrest, respiratory arrest, coma, etc. In addition, the symptoms of cerebral herniation, as a result of intracerebral masses, they develop quickly because they cause acute structural changes. In particular, in cases where the uncus is involved, there is usually homolateral dilation of the pupil (by compression of the oculomotor nerve), pupillary paralysis (or myosis) and drowsiness. The evolution towards coma is characterized by Cheyne-Stokes breath and one-sided decerebration rigidity. The central syndrome may in some cases also represent the evolution of a uncal syndrome, by secondary compression of the trunk and is characterized by a progressive deterioration of brain functions: confusion, apathy, drowsiness, Cheyne-Stokes breath, Pupillary hyporeactivity usually in myosis, early bilateral Babinsky sign and, later, coma, with decerebration symptoms. In the case of cerebellar hernias there will be decerebration posture and first myosis, then fixed midriasis, while transfalcial hernias often cause occlusion of the anterior cerebral artery with cerebral infarction in the frontal lobe.

From an anatomical point of view, cerebral hernias can occur at any level of the central nervous system, for example, Arnold-Chiari malformations are associated with a cerebellum herniation.

In neurosurgery, decompressive craniectomy, a surgical procedure that involves the removal of a large section of the skull and a part of the dura mater that is then replaced with a dural substitute, allowing to increase the intradural space (incremental duroplasty) and consequently lower the intracranial pressure. However, this surgical procedure is highly invasive. For this reason, it is considered as the last therapeutic opportunity when a brain pathology determines a significant increase in pressure inside the cranial case, not controllable with medical therapy and that puts the patient's life at risk.

SUMMARY

It therefore exists in the specific sector the need for a procedure and/or a device for neurosurgery that can intervene with less invasiveness in diseases due to a brain hernia.

This requirement is satisfied by the device according to the present invention which also offers further advantages that will become clear later.

In this context, the solution according to the present invention, which aims to make less invasive interventions possible than the decompressive craniectomy, to solve the serious emergency that this pathology represents in the neurosurgical and neurological field. In fact, through the use of this device, the surgical procedure becomes the first choice of surgery and not the last possibility to save the patient.

In addition, the device according to the present invention can be used as a first choice tool to intervene on cerebral herniation, as a supporting surgical instrument in case of other neurosurgical intervention already started or, In addition, as a diagnostic tool for suspected cerebral herniation, allowing in the latter case rapidity of intervention and opportunity to gain valuable time for the neurosurgeon and the patient.

In addition, this surgical device can reduce swelling, protect cerebral homeostasis, eliminate excess/waste substances such as blood and transmit chemical and electrical signals.

These and other results are obtained according to the present invention by proposing a device that can compress and contain brain tissue and continuously monitor the patient's parameters.

The aim of the present invention is therefore to provide a device that will allow the limits of the known technology to be overcome and to obtain the technical results described above.

Another aim of the invention is that this device can be made with substantially low costs, both in terms of production costs and operating costs.

Not the last aim of the invention is to propose a device that is simple, safe and reliable.

Therefore, a specific object of the present invention is a surgical device for cerebral herniation comprising:

- a structure having a shape to cover the skull cap, this structure comprising a first portion, adapted to provide the structure with its shape, a second portion, adapted to be in contact with the cerebral parenchyma, and a plurality of tubular canals, said tubular canals forming a lattice that subdivides said surgical device in areas corresponding to the respective areas of the cerebral surface,
- a plurality of sensors attached to said second portion of said structure and in contact with the cerebral parenchyma, said sensors being adapted to monitor one or more parameters of the brain,
- an outflow system comprising at least one drainage catheter and means of connection to an aspiration system, said outflow system being positioned along the perimeter of said structure and being adapted to convey waste liquids or blood outside.

According to the invention said plurality of tubular canals may comprise a plurality of administration canals, said tubular canals comprising an inlet extremity of one or more drugs and an outlet extremity for the release of said one or more drugs into the cerebral tissue.

In particular, according to the invention, said plurality of tubular canals may comprise a plurality of aspiration canals connected to this outflow system, said aspiration system comprising a plurality of aspiration pumps.

Furthermore, according to the invention, said plurality of sensors may comprise fluorescent biosensors, said sensors being coated with an ultra-bright and stable biocompatible fluorescent coating, for illuminating one or more areas of the said surgical device, in particular corresponding to areas of the brain wherein said sensors determine the presence of an oedema.

More specifically, according to the invention, said structure may comprise a first and second level of tubular administration canals, said first level comprising a first plurality of canals parallel to each other and said second level comprising a second plurality of canals parallel to each other and perpendicular to said first plurality of canals.

Still, according to the invention, said surgical device can be made of 3D printed biocompatible polymers.

In particular, according to the invention, said first portion of said structure can be made of bioceramic material, said second portion of said structure can be made of hydrogel and said tubular canals can be made from a fibrous structural protein or silk.

Moreover, according to the invention, said bioceramic material can be chosen from alumina, or zirconia, or a ceramic polymer composite of poly-ε-caprolactone (PCL) and calcium β-tri-phosphate (TCP).

In particular, according to the invention said hydrogel can be a combination of polyethylene glycol (PEG) and poly 2-hydroxyethyl methacrylate (pHEMA).

Moreover, according to the invention, said sensors can comprise at least one transducer of a neural interface, said transducer being adapted to register the impulses of a neuron.

BRIEF DESCRIPTION OF THE DRAWINGS

The present invention will now be described, by way of non limiting illustration, according to a preferred embodiment, with particular reference to the figures in the appended drawings, wherein.

DETAILED DESCRIPTION OF THE EMBODIMENTS

With reference to the figures, a surgical device or helmet according to an embodiment of the present invention is indicated with the reference numerical 1.

This surgical device 1 comprises a structure having a first portion in contact with the outside and a second portion in contact with the cerebral parenchyma. In addition, this structure comprises multiple tubular canals 2 that allow the passage of drugs to the brain.

Figure 1:
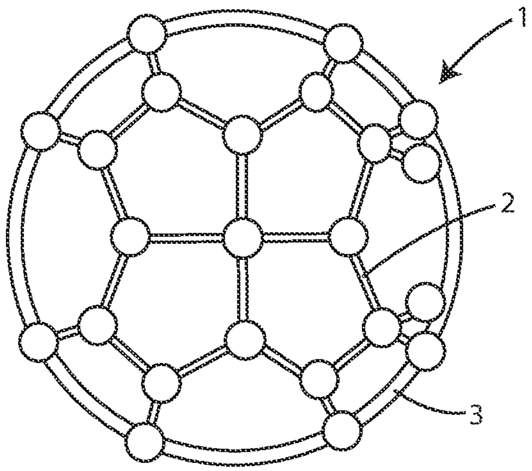
FIG. 1 shows a top view of a surgical device according to the present invention.

In a first embodiment, shown in FIG. 1, this surgical device 1 comprises a "honeycomb" reticular structure.

Figure 4:
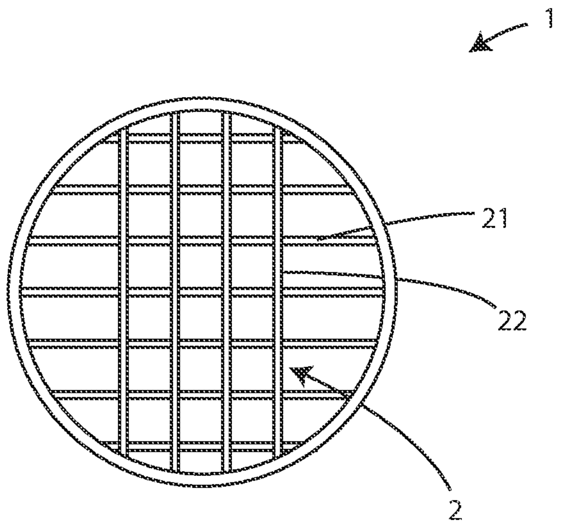
FIG. 4 shows a top view of a second embodiment of the present invention.

In a second embodiment, shown in FIG. 4, this reticular structure comprises two levels of tubular canals 2.

Figure 3:
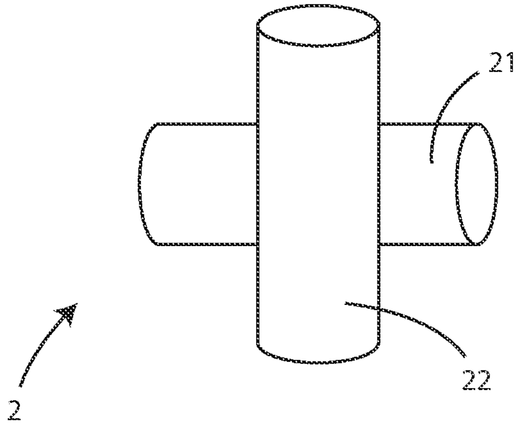
FIG. 3 shows a top view of two tubular canal of the device in FIG. 1.

In particular, a first level formed by a first plurality of canals 21 parallel to each other and a second level formed by a second plurality of canals 22 parallel to each other and perpendicular to those canals 21, as shown in FIG. 3. The first level can be placed above or below the second level.

In addition, the arrangement of such tubular canals 2 allows a subdivision of this surgical device 1 into areas corresponding to respective areas of the brain surface.

In addition, these tubular canals 2 function as selective ion canals equipped with a selectivity filter.

In particular, each tubular canal 2 comprises two extremities, an inlet extremity 2' of the aforementioned drugs and an outlet extremity 2" of said drugs, said two extremities being placed respectively outside and inside the skull. In addition, each tubular canal 2 comprises, at least at one of the two extremities, a permanent and fully implantable central venous access device, or a port-a-catch to allow the entry and exit of pharmacological substances. This central venous access device consists of a catheter made of biocompatible material, such as silicone, a chamber and a tank. In particular, a special needle is inserted in this chamber, for example the Huber needle, which with its shape allows to pierce the chamber without damaging it. In addition, these pharmacological substances must enter and exit these tubular canals 2 separately from each other and must act synergistically only at the point of release of the same.

Figure 2:
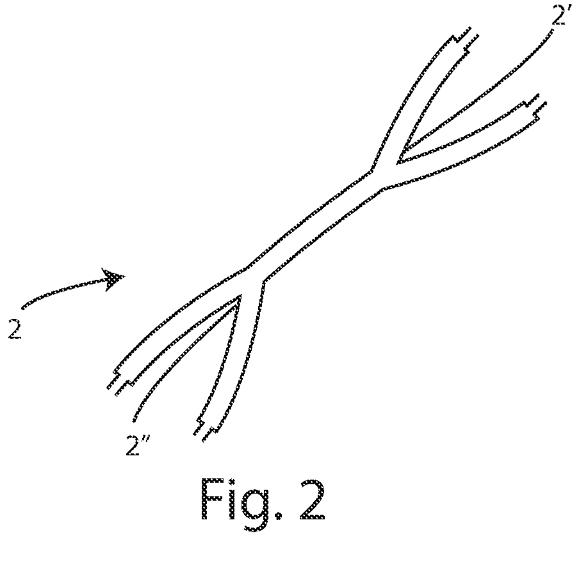
FIG. 2 shows a perspective view of a tubular canal of the device in FIG. 1.

FIG. 2 shows a tubular canals 2 comprising an inlet extremity 2' and an outlet extremity 2".

In particular, said inlet extremity 2' of each tubular canals 2 comprises a deflussor. This deflussor comprises:

a bayonet or perforator for piercing the drip cap, a drip chamber located below the perforator, this chamber allows the flow of the solution drop to be controlled and is equipped with an air valve with antibacterial filter and air inlet device, a clamp or flow regulator comprising a wheel positioned in a track, known as a wheel, which allows the opening, closing of the drip chamber and the adjustment of the flow rate of the solution, a connector located at the end of that outflow, this connector allows the outflow to be connected to the venous route, by means of a luer lock system or a component that allows the connector to be screwed or by means of a cone system, and a circular tube of length between 145 and 200 cm.

This deflussor is controlled manually by the surgeon who injects the substances and is adapted to be attached to the device for central venous access.

In addition, each inlet extremity 2' comprises two different inlets for the different substances.

In addition, the outlet extremity 2" of each tubular canal 2 is in contact with the cerebral parenchyma and comprises two outlets to allow a direct release of pharmacological substances to the brain tissue.

In other words, the two inlet 2' and outlet 2" extremity comprise two tubular canals that flow into this tubular canal 2.

The biggest obstacle to targeted drug delivery is having to overcome the blood-brain barrier. If direct administration to the brain is not possible, substances could also be released into the brain parenchyma encapsulated in biocompatible and biodegradable transporters.

As an example, nanoparticles could be used, which represent ideal vehicles for drugs that can be encapsulated within the particle or directly released onto the brain surface by absorption or binding to the polymer itself. The use of biodegradable nanoparticles as carrier molecules is one of the most promising strategies for the development of controlled release systems. The basic requirement is the biocompatibility of the material, namely its ability to be metabolized without harmful effects.

Therefore, in the event that the direct release of drugs is not suitable for the type of intervention, biopolymers can be used. However, the functioning of the tubular canals 2 is the same, with the difference that drugs, instead of being injected and released directly, should first be incorporated into biotranscarrier and then injected and released through such tubular canals 2.

In particular, in the vertical canals 22 of this second level a noncontinuous solution of mannitol can be released, while in the horizontal canals 21 a corticosteroid solution can be released. The possible choice of using mannitol and corticosteroids is due to their pharmacokinetic characteristics, which can reduce edema and counteract inflammation. In particular, corticosteroids are classified according to the main effects in glucocorticoids and mineralocorticoids.

Glucocorticoids provide anti-inflammatory responses by suppressing inflammation and immunity, exert a vasoconstrictive action; mineralocorticoids show salt retention and electrolyte balancing properties. Currently they represent the most widely used category of drugs, they can be used to treat various conditions such as infections, inflammatory disorders, allergic and autoimmune diseases, shock, lowering of excessive levels of calcium in the blood, hypoglycemia, suppression of excess secretion from the adrenal cortex, prevention of transplant rejection, neurological disorders, haematological disorders, skin disorders, etc. In addition, dexamethasone, prednisone, prednisolone and methylprednisolone have advantageous characteristics that make them suitable for different clinical applications, e.g. treatment of patients with carcinomatous meningitis. The binding of the free glucocorticoid receptor leads to the release of a 90 kda thermal shock protein which in turn exposes two nuclear localization signals responsible for facilitating the movement of the glucocorticoid-receptor complex in the nucleus. GRE (glucocorticoid response elements) regulate the transcription of nuclear DNA. The synthesis of several cytokines and chemokines involved in the regulation of inflammatory reactions is suppressed by glucocorticoids at the transcription level. In addition, the interaction of glucocorticoids with other transcription factors such as p53 indirectly affects their activity on target genes.

Therefore, inhibition of NF-κB transcription factors, CRE bound proteins, etc. induces anti-inflammatory responses. Corticosteroids bind to intracellular cytoplasmic receptors after crossing the plasma membrane, forming the steroid-receptor complex. As a result, the movement of the steroid-receptor complex in the nucleus directly affects the transcription of genes. They are often prescribed to reduce the increase in intracranial pressure caused by the accumulation of fluid. A disruption of the blood-brain barrier leads to the flow of fluid into the extracellular spaces of the cerebral parenchyma resulting in vasogenic edema. This interruption results in increased permeability of the blood-brain barrier mainly due to the opening of narrow interendothelial junctions and increased endothelial pinocytosis and endothelial fenestrations. The main mechanism of action of corticosteroids reduction of permeability of damaged cerebral vessels by over-regulation of genes and molecules. A second mechanism aimed at influencing endothelial permeability is the non-transcriptional regulation of capillaries that involves rearrangement and attachment of endothelial vascular cadherin (VE) to the cytoskeleton.

Then, with the administration of corticosteroids the permeability of the blood-brain barrier decreases, limiting the sprain of fluids.

In addition, mannitol is a sugary alcohol ($C6H14O6$) that decreases the reabsorption of water and sodium, used to reduce intracranial pressure and/or cerebral edema since the 1960s. Mannitol reduces intracranial pressure by decreasing blood viscosity and promoting plasma expansion with the release of cerebral oxygen leading to cerebral vasoconstriction due to self-regulation with reduced blood volume. In addition, it creates an osmotic gradient through the blood-brain barrier that leads to the movement of water from the parenchyma to the intravascular space. The volume of brain tissue is thus decreased along with intracranial cerebral pressure. Mannitol also acts as an osmotic diuretic, leading to the free elimination of water and increased serum osmolality. As a result, water moves from intracellular to extracellular space, inducing a prolonged dehydrating effect.

In particular, the concentrations and times of release of these drugs are variable with the conditions in which the herniated brain is involved.

In addition, in tubular canals 2 heparin can be released.

In addition, said surgical device 1 comprises:

an outflow system 3, and a plurality of sensors.

This outflow system 3 comprises a tubular structure and is positioned along the perimeter of that reticular structure of that surgical device 1. In addition, this outflow system 3 is adapted to convey waste or excess substances out of the brain. In particular, these substances are liquids that accumulate in the brain during cerebral herniation such as:

- edematous or exudated fluid from blood vessels composed predominantly of plasma, called fluid compresses blood capillaries and skull walls causing a blockage in the supply of oxygen and nutrients, slowly leading to necrosis of brain tissue, and
- CSF or CSF that may remain confined to the cerebral ventricles leading to excessive accumulation of CSF within the brain.

In particular, this outflow system 3 compresses at least one silicone drainage catheter that perimeter the helmet and penetrates the surgical site at the intracranial level, at the ventricles of the brain, when the device is applied after cranioresezione.

In addition, the outflow system 3 is connected by means of an extension to a bellows container capable of exerting a slight suction and by means of a feeding tube to a suction pump system external to that surgical device 1. In addition, said bellows container is connected to a graduated emptying bag, from 0 to 600 ml, in which the liquid can be drained and measured. In addition, this emptying bag comprises a tap for emptying at the bottom of the bag. Furthermore, this emptying bag includes an anti-reflux valve to form a unidirectional circuit in which the drained fluid does not return back. Such a system is necessary to avoid excessive drainage potentially dangerous for the patient. Then, the fluid is drained from the ventricular chambers and the valve controls its flow.

In particular, this pump system comprises one or more volumetric piston or piston pumps. In these pumps the volume variation is obtained by the alternating flow of a piston in a cylinder and appropriate check valves that force the liquid to flow in only one direction preventing the reflux during the return stroke of the piston. In this case the pump has a double effect because the piston performs work both on the outward and return. This type of pump offers great design flexibility, variety of sizes and piston resistances that, combined with the adjustable displacement characteristics, integrated into the pump head, allow for extensive design flexibility. In addition, such pumps may comprise sensors to monitor speed, temperature, and pressure/vacuum.

The combination of these features results in a long-lasting fluid intake system. In the suction action, the piston causes a depression, which causes the lifting of the liquid along a pipe and its expulsion from the pump at ambient pressure. With the pressing action, the fluid enters the cylinder at room pressure and the pump is lifted by pressure. In this case, the cylinder is located at the same level or below the liquid to be lifted.

In addition, the pump comprises a drive motor which may be internal or external to the pump. The pump has a central cavity, in which the fluid is sucked and expelled by the movement of the piston. This movement has a direct influence on performance, although it is limited by the power of the drive motor and the number of revolutions the pump can start. Flow and pressure are affected by the size of the pump. In fact, to a small area of the pump cavity will correspond to a higher pressure and lower flow rate; on the contrary, to a larger area of the cavity will correspond an increase in the flow rate and a decrease in pressure. The pumping action provides precision and repeatability for long periods of operation. The pump, with medium viscous fluids, also benefits from good control and constant flow rates, while with variable viscosity fluids it maintains a good flow rate and can withstand medium-high pressures. The limits of the pressing pump are due to the problems of containing the high pressure by the pump chamber, seals and valves. A possible solution to overcome their limitation could be to adopt piston pumps without valves. The immediate advantage is that there are fewer moving parts that wear out or break, thus improving both durability and chemical compatibility. The technology is based on the movement of a "split" dovenest piston that serves to block the entrance and exit while moving back and forth in the chamber.

In conclusion, these suction and pressing pumps allow the removal of excess fluid that can aggravate the pathological picture of the patient.

In a preferred embodiment, said outflow system 3 comprises four suction pumps:

- a first suction pump located at the front pole,
- a second suction pump located at the occipital pole, and
- a third and a fourth suction pump located at each temporal lobe.

In addition, this surgical device 1 comprises multiple sensors arranged at the bottom of the surgical device 1 in order to be in contact with the cerebral parenchyma. Even more specifically, these sensors are anchored on one side to the internal interface of the surgical device 1 that penetrates the cerebral parenchyma, that is, to the second portion of that structure, and on the other deepen into the neural tissue. This plurality of sensors offers continuous monitoring of parameters such as cerebral perfusion pressure, cerebral blood flow, temperature, partial pressure of O2 etc. Furthermore, these sensors are sensitive to changes in blood composition and to changes in pressure, temperature and solutes in brain metabolism. In addition, these sensors are adapted to penetrate deep into the brain, so as to also detect the parameters of structures such as the cerebellum and the brainstem. In addition, these sensors must be completely biocompatible and have a functioning similar to that of chemoceptors or must be able to signal endogenous change in the composition of circulating liquids.

In a preferred embodiment this plurality of sensors comprises eleven sensors positioned as follows: two at the front pole, two at the parietal pole, two at the occipital pole, two in correspondence of the temporal pole, two in correspondence of the lateral furrow, respectively one on the right and one on the left, and one in correspondence of the central furrow.

Moreover, this plurality of sensors comprises a lighting system to signal the precise point of the entire brain where there is edema and it is therefore necessary to intervene through the release of pharmacological substances to counteract the pathological phenomenon in progress. In this way, the sensors analyse the condition of the organ and indicate anatomically to the surgeon where it is necessary to intervene, illuminating the respective area of the surgical device 1. Such illumination occurs thanks to the materials of said surgical device 1.

As is known, fluorescence is the property of some molecules to absorb light at a certain wavelength and emit light at a greater wavelength. The use of fluorescence in the clinical environment has always been considered a fundamental tool for rapid, non-invasive, selective and sensitive diagnosis. The near-infrared coating of equipment (NICE) was synthesized by combining a biocompatible poly methylmethacrylate (PMMA) polymer with a specially designed fluorescent dye.

Thus, the sensors of said surgical device 1 are coated with an ultra bright and stable biocompatible fluorescent coating (NICE). Said coating can be viewed using commercially available surgical NIR cameras.

This coating in the near infrared involves the synthesis of a series of dyes of the cyanine-7.5 family, including long lipophilic alkyl chains, rigid conjugation chain and some voluminous groups to optimize solubility and brightness in the polymer matrix, offering a bright and stable coating, compared to losses in biological media with ICG (indocyanine green fluorescent coatings). In addition, cyanins with rigid conjugation chain also show increased photo stability.

In addition, to improve rigidity, the polyethylene chain was reinforced by a cyclohexane ring to improve their chemical and photochemical stability. To minimize the damage caused by aggregation, some of the dyes have been modified with bulky phenyl groups. Finally, since all the Cy7.5 dyes developed are cationic, their small inorganic anionic iodide has been replaced with a bulky hydrophobic tetraphenyl borate (TPB) counterion.

In fact, voluminous anions can prevent secondary adverse reactions caused by aggregation and ensure a good loading of the dye into the polymer matrix.

In addition, this coating can be deposited on a variety of materials, such as glass, metal and polymer, using different techniques, including immersion coating and rotation coating.

This coating uses light in the NIR range, that is, with a wavelength in the 650-900 nm range, which has many advantages over visible range light, including deeper tissue penetration due to lower absorption of hemoglobin and water. In addition, NIR coatings are biocompatible and non-toxic.

In addition, this NICE coating is compatible with the standard sterilisation protocols based on ethylene oxide and steam and is biocompatible, without signs of cytotoxicity. In fact, the use of NICE on several medical devices for image-guided surgery in models of pig and human cadavers has already been validated.

However, the use of this coating provides that the lights in the operating room must be turned off during the acquisition of fluorescence. Additionally, this bioluminescence can be acquired using an IVIS spectrum system.

In particular, these sensors can be luminescent or fluorescent biosensors, that is, sensors that allow to monitor the chemical transmission in vivo with extreme precision and analyze the behavior of a single cell. Changes in the luminosity of the fluorescent biosensor occur as a result of binding to the neurotransmitter and can be detected using fiber photometry, stationary microscopy, and/or miniature microscopes mounted on the head.

To develop a fluorescent biosensor to investigate the health/activity status of the nervous tissue, a pair of FRET (fluorescence resonance energy transfer) is combined of fluorescent proteins FP or a cpFP or fluorescent proteins of the cyanine family, with a respective binding protein, called the detection domain.

In one embodiment, this surgical device 1 comprises FRET-based biosensors using Cy5.5 as a donor on a filament and Cy7.5 as an acceptor on the complementary filament in order to detect and characterize the NF-kappaB p50 transcription factor. The nuclear factor NF-κB belongs to a family of key transcriptional factors composed of five members in mammalian cells, including NF-κB1 (p50), NF-κB2 (P52), rela (p65), RelB and c-Rel. NF-κB is involved in multiple physiological and logical processes, including cell proliferation and differentiation, inflammatory and immune response, cell survival and apoptosis, cell stress reactions and tumorigenesis.

Integration with biosensors can bring many advantages, for example, it can allow automated monitoring of a wide range of analytes and biomarkers, later making the surgical device 1 also suitable for a personalized study of diseases or drug testing in diseases of the nervous system.

In addition, the sensors are connected to a wireless transmitter and the detected signals are read via an electronic board. Once the information is acquired, through an integration process, it is sent to an external monitor (screen) in front of the neurosurgeon.

In addition, these sensors can be wireless brain sensors, composed of biocompatible metals, e.g. magnesium, titanium and zinc, which act as conductive elements, with polylactic co-glycolic acid biopolymers and allow constant monitoring of brain electrical activity (in the form of "brain waves" that reflect electrical transmission within the brain) and to detect pressure, temperature and pH within the brain. The wireless technology of these sensors ensures continuous signal reception and data transmission from the brain to external analysis devices. The use of these brain sensors must be incorporated with wireless microelectrodes (MEA) that placed on the side of the cerebral parenchyma are adapted to penetrate it. Obviously the substrate of the microelectrode must be flexible so as not to cause trauma, inflammation, etc. to the cerebral parenchyma. The substrate of said microelectrode can be a biodegradable polymer such as polylactic acid-co-glycolic, able to move like a second skin on the brain tissue, without causing trauma, in response to changes in pressure of the fluid surrounding the organ.

Using a neural network interface comprising at least one electrode or transducer with a diameter of approximately 20 μm, it is possible to record the pulses of a single neuron and observe the action potentials of the brain surface, with wireless data transmission, so as to be able to simultaneously detect information on the electrical state (such as a kind of EEG) of nerve cells and changes in biochemical parameters, pressure, temperature, composition, etc. of the organ in question.

In particular, neural interfaces record electrical nerve signals, putting in direct communication the brain and an external device to the parenchyma.

Surgical device 1 has a bi-directional interface that combines the direct reception of information from brain activity with a return line that allows the exchange of information between the device and the brain. These neural interfaces involve three main processing processes:

- a signal processing phase in which the data recorded by the transducer is pre-processed,
- an extrapolation phase of the characteristics, in which the significant neural information is extracted from the recorded data,
- a classification phase, in which the intention of a user is decoded by the neural data. In addition, the acquired signals such as electroencephalogram, functional magnetic resonance, positron emission tomography, magnetoencephalography, near infrared functional spectroscopy, etc.

Signals are sent as data to the transducer for which the acquisition devices are placed inside the transducer box. The transducer output corresponds to a classification target and represents the identification of the brain pattern. Hence, the control interface is responsible for collecting output data sequences from the transducer and encoding them into semantic symbols. The logical alphabet then represents the contact between a transducer and a control interface, so that different transducers and control interfaces can be combined and matched provided their logical alphabets are compatible. In particular, neural interfaces use different neuroimaging methods to acquire their own brain signals, generally classified according to their invasiveness, spatial/temporal resolution, direct/indirect measurement and complexity/price. Neural interface recording methods are divided into invasive and non-invasive.

Non-invasive recording methods are neuroimaging techniques in which sensors are placed on the scalp and are prevalent used two types:

Direct measurements: detect electrical (EEG) or magnetic (MEG) brain activity indirect measurements of brain function: they reflect brain metabolism and/or brain hemodynamics, such as functional magnetic resonance imaging (fMRI), near-infrared functional spectroscopy (fNIRS) and positron emission tomography (PET).

Direct brain monitoring approaches typically provide detailed information with high temporal resolution, but usually lack spatial coverage, while indirect measurements show higher spatial resolution than direct measurements.

Thus, in the case of the surgical device 1 for cerebral herniation, using non-invasive methods of registration of the neural interface, combining direct and indirect measurements, it will be possible to operate an anatomical scan, electrical and metabolic of the brain allowing the acquisition of combined information without having to resort, during surgery, to different methods of neuroimaging and brain analysis. The surgical device 1 so designed wants to unify aspects and methods of neuro-investigation.

Invasive recording approaches include, instead, two types of recording methods: electrocorticography (ecog) and intracortical neuron registration (INR). During the acquisition of signals, an overlap of information may occur, in which extraneous "raw" signals, known as artifacts, hinder the performance of the neural interface and it is therefore important to remove them. A possible solution to increase sensitivity to particular brain sources and improve their localization could be obtained by including filtering methods. Feature extraction is the process by which relevant aspects of the signal are distinguished and identified from raw neural data, e.g. a potential event-correlated, that is variations of the electric potential deriving from a visual stimulus, somesthetic or auditory external that represent modifications of the spontaneous cerebral electrical activity; a negative correlated event, related to a potential related event, is a strong negative signal that starts at about the same time as a wrong motor response is triggered and has been mainly attributed to activity in the anterior cingulate cortex, etc. The main objective of feature extraction is to facilitate the identification of models and improve the accuracy of the neural interface while reducing the dimensionality of the data.

In addition, the neural interface system of the surgical device 1 must combine the accuracy of the classification of nerve signals and the ability of the control interface to prevent and/or correct errors. The contributions of the transducer and the control interface must be communicated separately, thus enabling the differentiation of performance between the ability to detect brain models and the optimization of the coding of logical alphabets in semantic alphabets.

Moreover, taking into account the anatomical delicacy of the organ on which this device will have to work it is good to specify that the entire operation of the device and therefore also that of those sensors, must be as similar as possible to the physiological functioning of the human brain, this to allow the maintenance of the vascular system and not cause further trauma (in addition to the pathological event already underway) once the device is applied.

In particular, these sensors include electronic components, such as field effect transistors that, by detecting the chemical of interest, produce an electrical signal that can be detected and analyzed outside the body. However, such sensors should only respond to specific chemicals of interest and ignore the crosstalk of other biomarkers, In other words, the sensors must be able to detect changes in brain fluids while the electronics present in the sensors must be protected by these same fluids. This is achieved with an impermeable encapsulation of the sensor, with a thin film of silicon dioxide, forged at temperatures above almost 2000° F.

In one embodiment, these sensors can be made on a 3D microelectrode matrix with a flexible substrate, as they are easy to fabricate, perfectly compatible with tissues and do not require invasive anchoring techniques.

In addition, in a preferred embodiment said surgical device 1 is made by 3D printing of biocompatible materials since said surgical device 1 must ensure the containment and reduction of cerebral swelling.

In fact, this surgical device 1, precisely because in close contact with the cerebral parenchyma, must be made with biocompatible polymers with brain tissue, and must be elastic and compressive and at the same time capable of transferring electrical and chemical signals.

In addition, the material with which it is made said surgical device 1 must be resistant to heat and impact and with high conductivity (for electrical and chemical signals), this to remedy the problem of incompatibility between this surgical device 1 and the mechanical properties of the brain. Instead, elasticity is crucial to not having to exert excessive pressure on the surface of the brain that could cause inflammation and nerve destruction.

In addition, the choice of biocompatible material must take into account the fact that changes in brain size may occur during surgery (different from individual to individual and depending on the extent of the pathological event) which is why the material of realization cannot be rigid and not very ductile.

In addition to this, the surgical device 1 must function as a device of anatomical scanning and brain activity to allow the neurosurgical a complete acquisition of biochemical and anatomical information of the brain (as a kind of functional MRI).

The choice to use biocompatible polymers is due to the fact that these materials, natural and/or synthetic, can work in close contact with living tissues and are also able to replace a part of organic tissue because, through appropriate tests, non-toxicity is ensured for the organism.

In fact, natural polymers have better biocompatibility and bioactivity, while synthetic or non-natural polymers have better mechanical properties and structural stability. The combination of the two polymers allows you to create a medical device that can mimic the physiological environment of neural tissue that does not damage nerve structures. In addition, all products made with biopolymers and 3D printer can be sterilized, and the method of sterilization varies depending on the choice of material.

In neural tissue engineering, the use of synthetic or non-natural polymers offers numerous advantages, mainly due to their flexibility, mechanical strength and ease of modification and customization. These structural properties enable customised processing with different modification techniques, including mixing and copolymerisation. In addition, synthetic polymers are also compatible with numerous manufacturing techniques, such as wet spinning, freeze-drying and electrospinning. Some synthetic polymers, despite being non-toxic, still create some concern for degradation products, plasticizers, etc.; therefore the tests required before being used in the clinic must be complete.

In a preferred form of construction, the first portion of the surgical device 1 is made of bioceramic materials, while the second portion of the surgical device is made in contact with the cerebral parenchyma, is hydrogel, both obtained through 3D printing.

In particular, bioceramics are a known class of materials used in biomedical applications due to their mechanical stability and excellent biocompatibility. To these characteristics is added their potential for bioactivity, the great freedom of design in the design phase, the resistance to acids, alkaline solutions and heat, the high elasticity at high temperatures, gas-proof and cost-effective solution for the production of individual components. Alumina and zirconia are among the most commonly used bioceramics; are high density materials with great mechanical and corrosion resistance. It is reported in the literature that zirconium oxide is slightly less resistant than alumina to corrosion. Both bioceramics are biocompatible and bioinert and can provide structural support preventing stress protection and avoiding tissue reactions adverse to ionic toxicity from stents or metal prostheses.

In another embodiment a ceramic polymer composite of poly-ε-caprolactone (PCL) and β-tri-calcium phosphate (TCP) is used, created through the extrusion method of additive production, which has a high degree of biocompatibility with a compressive strength of up to 90 Mpa.

A limitation that could represent the choice of bioceramics as covering material of the surgical device 1 is given by their shrinkage after sterilization. However, by considering selective laser sintering to melt alumina and zirconia together, preheating the powder bed reduces thermal stress and helps prevent cracks and limit distortion by solving this problem. In addition, the use of binding materials can also contribute to the stabilization of the press and the sealing of the structure after debinding.

As mentioned, in a preferred embodiment the second portion of said structure of the surgical device 1 is made of hydrogel. Hydrogels are three-dimensional cross-linked hydrophilic polymer networks that can reversibly swell and de-inflate in water and can retain large volumes of liquid in a bulging state. They can give controllable responses and shrink or expand according to their environment. In addition, hydrogels can be designed and constructed in different shapes (2D or 3D). The conductive hydrogels based on natural biopolymers are renewable and non-toxic and have high biocompatibility, biodegradability, excellent flexibility and conductivity, showing great potential in wearable and extensible sensing device applications. However, conductive hydrogels consisting of continuous cross-linked polymer networks show a combination of superior elasticity and conductivity as their polymer networks give hydrogels mechanical flexibility. For example, biopolymers such as cellulose, chitosan, and silk fibroin are usually chosen as candidates for building conductive hydrogels, providing hydrogels with improved mechanical properties and remarkable biocompatibility. In neural tissue engineering, the two most commonly used polymers to create synthetic hydrogels are polyethylene glycol (PEG) and poly 2-hydroxyethyl methacrylate (pHEMA). The use of hydrogels, both PEG and pHEMA, in neural tissue engineering offers several advantages, including the variety and the fact that they can be applied as nerve guidance ducts, Intravenous inhibitors of cell death and as 3D structures that support the formation of nerve tissue. The range of complex applications achievable ensures the ability to adapt each polymer to a specific application, mimicking the environment of the host tissue.

For these reasons, in a preferred embodiment the second portion of said structure of said surgical device 1 is realized using in combination PEG and pHEMA.

PEG is a synthetic polymer biodegradable, biochemically inert, highly biocompatible and suitable for the realization of hydrogel due to its hydrophilic properties, crucial for the transport of nutrients and waste. However, PEG is not bioactive and is often used in combination with other polymers.

The use of PEG on neural cell growth platforms has shown that it improves survival, proliferation and differentiation, showing enormous potential for treating CNS lesions. After severe traumatic brain injury, intravenous administration of PEG dampened the loss of brain cells and slowed the degeneration of injured axons. In addition, PEG has shown promising results following spinal cord injury, significantly accelerating and improving the process of closing the membrane and restoring mechanical integrity after compression.

Polypyrrolol (PPy) is an organic polymer formed by polymerization of the pyrrole monomer and is one of the most commonly used conductive polymers in the engineering application of neural tissues.

One of the most interesting applications of PPy is its use as a new electrode material for chronically long-term implantable neuroprosthetic devices.

Recently, it has been shown that immersion of PPy in plasma limits adverse immune reactions and promotes direct tissue integration. This technique was used to create a biologically active electrostimulant neural interface. PPy has also found applications as an electrically controlled vehicle for the localized administration of drugs to the central nervous system.

In addition, the tubular canals 2 of said surgical device 1 are made of 3D printed biomaterials, e.g. silk, fibrous structural protein that has great mechanical strength, excellent biocompatibility, minimal immunogenicity, limited bacterial adhesion and controllable biodegradability. The combination of silk and electroconductive polymers has been shown to have good potential for peripheral nerve regeneration, indicating extreme compatibility. In addition, silk composite scaffolds or carbon nanotubes have shown excellent results in the bioengineering of neural tissue, promoting neural differentiation and acting as a supporting matrix for nerve tissue regeneration.

The primary use of this surgical device 1 is in the operating room, during a neurosurgical operation for cerebral herniation or during another neurosurgical operation where a possible cerebral herniation is expected. For example, this device may be used in cases where therapeutic intervention is required to prevent and/or counteract brain herniation such as:

- Patient with severe head injury, GCS (Glasgow Coma Scale)<9 and pathological brain CT (e.g. presence of hematomas and/or lacerated-contusive-edema foci), or
- Cerebral intracranial pressure >20 mmHg.

In addition, surgical device 1 is adapted to cover the entire surface of the skull, once exposed, after cranioresezione to be adapted to map and intervene in any anatomical point of the human brain since cerebral hernias can occur at any level of the central nervous system. This feature avoids a fundamental obstacle in neurosurgery, that is, the difficulty of surgically reaching any area of the brain.

In addition, said surgical device 1 can be used as a device for brain herniation applicable after craniectomy or cranioresection, with brain exposure. In particular, before the application of this surgical device 1, surgical resection or the incision of the entire cranial circumference must be carried out. Next, the surgical device 1 is placed directly on the brain, after the complete removal of the skull cap. In this way, resection is the only invasive procedure during surgery.

In fact, said surgical device 1 has a helmet shape, that is, it is suitable to cover the skull cap.

In other words, through the use of this surgical device 1, the neurosurgeon during the operation, has a complete reconstruction of the brain structure of the patient, obtained by brain scan (operated by the helmet itself) and to which are added the physiological parameters detected by the sensors. Thus, all information is available in real time and visible with better image resolution allowing the surgeon to reduce the margin of error.

This invention has been described as illustrative, but not limiting, according to its preferred forms of realization, but it is understood that variations and/or modifications can be made by experts in the field without leaving the relative scope of protection, as defined by the annexed claims.

The invention claimed is:

1. A surgical device for cerebral herniation, comprising:

a structure having a shape adapted to cover a skullcap, said structure comprising a first portion adapted to provide the structure with its shape, a second portion adapted to be in contact with a cerebral parenchyma, and a plurality of tubular canals forming a lattice that subdivides said surgical device in areas corresponding to respective areas of the cerebral surface, a plurality of sensors attached to said second portion of said structure and in contact with the cerebral parenchyma, said sensors adapted to monitor one or more parameters of the brain, and an outflow system comprising at least one drainage catheter and a connection to an aspiration system, said outflow system positioned along the perimeter of said structure and adapted to convey waste liquids or blood outside, wherein said plurality of tubular canals comprises a plurality of administration canals, said tubular canals comprising an inlet extremity of one or more drugs and an outlet extremity for the release of said one or more drugs into the cerebral tissue.

2. The surgical device according to claim 1, wherein said plurality of tubular canals comprises a plurality of aspiration canals connected to this outflow system and said aspiration system comprising a plurality of aspiration pumps.

3. The surgical device according to claim 1, wherein said plurality of sensors comprises fluorescent biosensors, said sensors are coated with a biocompatible fluorescent coating for illuminating one or more areas of said surgical device corresponding to areas of the brain wherein said sensors determine the presence of an oedema.

4. The surgical device according to claim 1, wherein said structure comprises a first and second level of tubular administration canals, said first level comprising a first plurality of canals parallel to each other and said second level comprising a second plurality of canals parallel to each other and perpendicular to said first plurality of canals.

5. The surgical device according to claim 1, wherein the device is made of 3D-printed biocompatible polymers.

6. The surgical device according to claim 1, wherein said first portion of said structure is made of bioceramic material, said second portion of said structure is made of hydrogel, and said tubular canals are made from a fibrous structural protein or silk.

7. The surgical device according to claim 1, wherein said bioceramic material is chosen from the group consisting of: alumina, zirconia, or a ceramic polymer composite of poly-ε-caprolactone (PCL) and calcium β-tri-phosphate (TCP).

8. The surgical device according to claim 6, wherein said hydrogel is a combination of polyethylene glycol (PEG) and poly 2-hydroxyethyl methacrylate (pHEMA).

9. The surgical device according to claim 1, wherein said sensors comprise at least one transducer of a neural interface, said transducer adapted to register the impulses of a neuron.

* * * * *